United States Patent [19]

Stein

[11] 4,371,697

[45] Feb. 1, 1983

[54] 3-[1-(HYDROXYMETHYL)-2-PHENYLE-THYL]-N-[(PHENYLAMINO)-CARBONYL]-SYDNONE IMINE

[75] Inventor: Reinhardt P. Stein, Audubon, Pa.

[73] Assignee: American Home Products Corporation, New York, N.Y.

[21] Appl. No.: 194,702

[22] Filed: Oct. 6, 1980

[51] Int. Cl.[3] .................. C07D 271/04; A61K 31/42
[52] U.S. Cl. .................................. 548/125; 424/272
[58] Field of Search ................................ 548/125, 121

[56] References Cited

U.S. PATENT DOCUMENTS 3,277,108  10/1966  Daeviker .......................... 548/125

FOREIGN PATENT DOCUMENTS 2028880  12/1971  Fed. Rep. of Germany .
2738022   6/1978  Fed. Rep. of Germany .
 329890   4/1972  U.S.S.R. .
 222370   8/1973  U.S.S.R. .

OTHER PUBLICATIONS

Olovyanishinkiva et al., "Khim. Geterotsikl Soedin," 2, 170–175 (1978) & 9, 1198–1203 (1975).
Yashanskii et al., "J. Med. Chem. 14, 1013–1015 (1957).
Kholodov et al., "Mater. Resp. Rasshir. Konf. Farmacol. Gruz," 2nd (1977), pp. 84–85.
Polgar et al., "Acta. Pharm. Huag.," 48, Suppl. 23–24, 1978.
Polgar et al., Xenobiotica 9, No. 8, 511–520 (1979).

Primary Examiner—Anton H. Sutto
Attorney, Agent, or Firm—Richard K. Jackson

[57] ABSTRACT

A compound of the formula:

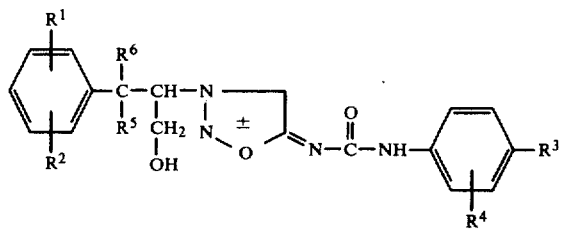

in which
$R^1$ and $R^2$ are, independently, hydrogen, alkyl of 1 to 6 carbon atoms, alkoxy of 1 to 6 carbon atoms, halo, perfluoroalkyl of 1 to 3 carbon atoms, nitro, alkanoyl of 2 to 4 carbon atoms or alkoxycarbonyl of 2 to 4 carbon atoms;
$R^3$ is hydrogen, halo, nitro or alkanoyl of 2 to 4 carbon atoms;
$R^4$ is hydrogen, halo, nitro or perfluoroalkyl of 1 to 3 carbon atoms;
$R^5$ and $R^6$ are, independently, hydrogen, methyl or ethyl;

or a non-toxic acid addition salt thereof, are central nervous system stimulants.

7 Claims, No Drawings

3-[1-(HYDROXYMETHYL)-2-PHENYLETHYL]-N-[(PHENYLAMINO)-CARBONYL]SYDNONE IMINE

BACKGROUND OF THE INVENTION

After the discovery of the central nervous system stimulatory properties of 3-(1-methyl-2-phenylethyl)-N-(phenylcarbamoyl)sydnone imine (Sydnocarb; U.S.S.R. 329,890 and Offenlegungsschrift 2,028,880) various analogues have been reported. U.S.S.R. 222,370 and Offenlegungsschrift 2,738,022 disclose sydnone imines which contain phenyl, 1- or 2-phenylethyl and the phenylisopropyl groups in 3-position as well as N-meta- and para-chlorophenyl and N-phenyl carbamoyl groups. Variations of 3-benzyl sydnonimines are disclosed in U.S. Pat. No. 3,277,108. Other variously substituted 3-aralkyl sydnonimines are disclosed by Olovyanishinkiva et al., Khim. Geterotsikl Soedin, 2 170–175 (1978) and 9 1198–1203 (1975).

Sydnocarb is conventionally produced by cyanomethylation of amphetamine followed by nitrosation and ring closure with a mineral acid to yield sydnophen as an acid halide salt which is reacted with phenylisocyanate under mildly basic conditions to introduce the N-phenylcarbamoyl group. As an asymmetric compound, amphetamine may be employed as the initial reactant as the racemic d,l-mixture or as the pure d- or l-isomer to yield racemic or optically active sydnophen and ultimately sydnocarb.

Yashunskii et al., J. Med. Chem., 14 1013–1015 (1971) disclose the marked CNS-stimulatory effect of 3-(1-methyl-2-phenylethyl) sydnonimine (Sydnophen). The relative activities of a large number of alkyl, aryl and aralkylsydnonimines are presented in Table 1 on page 1014. Most of them, including compound XVIII (2-hydroxy-1-methyl-2-phenylethyl-sydnonimine), were essentially inactive central nervous system stimulants relative to compound XIII (Sydnophen), demonstrating the criticality of the structure of the 3-substituent in the Sydnocarb series of compounds as far as CNS stimulatory activity is concerned. Thus, although the activity profile of Sydnocarb is not identical to that of amphetamine, or for that matter Sydnophen, CNS stimulatory activity is a common property of the initial reactant amphetamine, the intermediate Sydnophen and the final product Sydnocarb.

The metabolites of Sydnocarb have been studied by several groups. L. E. Kholodov and E. T. Lilin, Mater. Resp. Rasshir. Konf. Farmacol. Gruz. 2nd 1977, 84–5 report finding hydroxylation of Sydnocarb at the beta carbon of the phenylisopropyl substituent and at the phenyl ring of the phenylcarbamoyl group, hydrolytic cleavage of the phenylcarbamoyl group and ring opening of the heterocyclic nucleous. They report that the psychostimulating activity of Sydnocarb is a property of that compound and not its metabolites. Polgar et al. Acta. Pharm. Hung., 48, Suppl. 23–24 (1978) and Xenobiotica 9, No. 8, 511–520 (1979) report several hydroxylated metabolites and conjugates of hydroxylated Sydnocarb.

DESCRIPTION OF THE INVENTION

In accordance with this invention there is provided a group of central nervous system stimulants which are 3-[1-(hydroxymethyl)-2-phenylethyl]-N-[(phenylamino)-carbonyl]sydnonimines optionally substituted in either or both phenyl rings, of the formula:

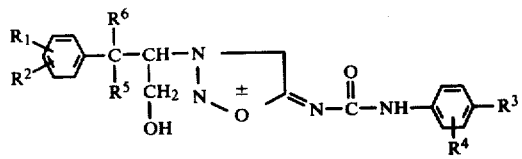

in which

R[1] and R[2] are, independently, hydrogen, alkyl of 1 to 6 carbon atoms, alkoxy of 1 to 6 carbon atoms, halo, perfluoroalkyl of 1 to 3 carbon atoms, nitro, alkanoyl of 2 to 4 carbon atoms, or alkoxycarbonyl of 2 to 4 carbon atoms;

R[3] is hydrogen, halo, nitro or alkanoyl of 2 to 4 carbon atoms;

R[4] is hydrogen, halo, nitro or perfluoroalkyl of 1 to 3 carbon atoms;

R[5] and R[6] are, independently, hydrogen, methyl or ethyl or a non-toxic acid addition salt thereof.

It is generally preferred that the halo substituent be chlorine, bromine or fluorine although iodine is acceptable. Likewise, it is preferred that the alkyl and alkoxy substituents be relatively small, the methyl, ethyl, propyl, isopropyl, methoxy, ethoxy, propoxy, and isopropoxy groups being preferred. The R[3] substituent in 4 position when R[4] is hydrogen influences potency to a greater extent than R[1], R[2] and R[4] and is preferably a halogen. The non-toxic acid addition salts of the compounds of this invention are conventionally produced by the method and from any of the acids disclosed in U.S. Pat. No. 3,277,108. The adduct products are preferably formed with hydrochloric, hydrobromic, sulfuric, phosphoric, acetic, propionic, oxalic, succinic or maleic acid.

The 3-[1-(hydroxymethyl)-2-phenylethyl]sydnonimine compounds of this invention contain one or two chiral centers at the benzylic carbon atoms depending upon the character of R[5] and R[6]. When R[5] and R[6] are hydrogen, activity resides primarily in the l-isomer although mixtures of the d and l isomers are active stimulants and the mixtures need not be separated for practical use applications.

Unlike Sydnocarb, the compounds of this invention are derived from phenylalaninol or an alkyl substituted derivative thereof through the intermediate 3-[1-(hydroxymethyl)-2-phenylethyl]sydnonimine or 3-[1-(hydroxymethyl-2-alkyl)-2-phenylethyl]-sydnonimine, none of which are known to demonstrate any central nervous system stimulatory activity. Being derived from reactants and through intermediates which are substantially devoid of activity, the compounds of this invention do not share with Sydnocarb the potential problem of degradative reversion or metabolic conversion back to a precursor which is itself active with a different pharmacological profile. Furthermore, handling of the inactive reactants and/or intermediates involved in this invention poses no problem for the production chemist.

The activity profile of the compounds of this invention is similar to that of amphetamine in some aspects while being devoid of other activities of amphetamine. For example, like amphetamine the compounds of this invention increase motor activity. However, the compounds of this invention are much less toxic than amphetamine, providing a slower onset of activity (which indicates less euphoria and abuse potential).

The compounds of this invention were shown to possess central nervous system stimulant activity by subjecting them to the following standard test procedure.

Male mice weighing 17 to 25 gms. are injected orally with drug, solubilized or suspended in 1% Tween ® 80. Control animals are injected with 1% Tween ® 80.

Six Columbus Instrument Company activity chambers are employed. Three mice given identical treatment are placed in each chamber for all tests. During each run, control animals (1% Tween ® only) occupy 3 chambers; the other 3 chambers measure activity of drug treated animals. For each dose of a given drug the experiment is run two times in a counterbalanced design so that each specific activity chamber records the activity of control animals during one run, and the activity of drug animals on the other run. Thus at each dose level 18 mice are used in the drug group and 18 mice in the control group.

Activity counts are recorded every ten minutes for a period of 2 hours. The data are analyzed using Students "t" test comparing the means of the control and drug groups for each 10 minute period. The drug treated group is compared graphically with the control group in regard to duration of action and dose response at peak drug activity.

As central nervous system stimulants with unique activity profiles, the compounds of this invention are useful in the treatment of anergic disorders (such as sleepiness and fatigue) including related types of depression and narcolepsy. Based upon the potency of the compounds of this invention in use in mice, the dose contemplated for use in the 70 kilogram human would vary from about 35-700 milligrams administered orally once or twice per day under the guidance of a physician. Of course, the dosage regimen as well as the route of administration, oral or parenteral, will vary with the condition of the patient relative to age, severity of depression, etc.

The compounds of this invention are prepared by conventional techniques analogous to those employed in the preparation of Sydnocarb. Thus, a properly substituted phenylalaninol is cyanomethylated with a reactant $XCH_2CN$ where X may be —OH, —Br, —Cl, tosyl, and the like to form the intermediate

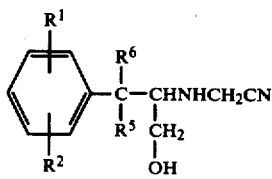

which is nitrosated with an excess of $NaNO_2$ in aqueous HCl to yield

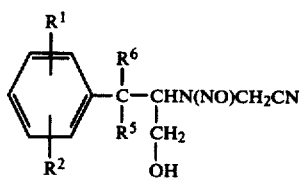

which upon treatment with HCl (anhydrous or in an alkanol, preferably isopropanol) yields the sydnonimine salt

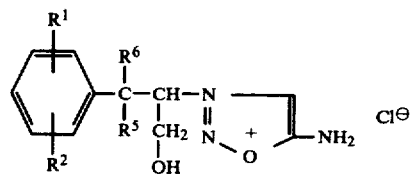

which when reacted as an alcoholic suspension (methanol, ethanol, isopropanol, etc.) with

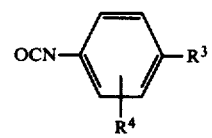

in the presence of a mild base such as sodium acetate yields the desired 3-[1-(hydroxymethyl)-2-phenylethyl]-N-[(phenylamino) carbonyl]-sydnonimine derivatives. The mild base releases the reactive sydnone free base

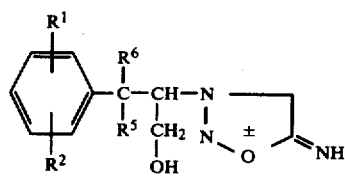

which readily undergoes nucleophilic addition to the isocyanate reactant.

The following examples illustrate without limitation the process for producing the compounds of this invention. Where the intermediate cyanomethylated product of phenylalaninol and the N-nitroso derivative thereof are isolated as oils, no attempt was made to obtain the purified intermediate. The activity counts presented at the end of each example represent the difference from control based upon the test procedure disclosed, supra. l-Sydnocarb itself demonstrated a difference from control of 939 activity counts at 10 mg/kg., p.o. and dl-Sydnocarb differed from the control by 636 activity counts at the same dose and route of administration.

EXAMPLE 1 dl-5-Amino-3-[1-(hydroxymethyl)-2-phenylethyl]-1,2,3-oxadiazolium chloride

Cover dl-2-amino-3-phenyl-1-propanol hydrochloride (31.4 g.; also as dl-phenylalaninol hydrochloride) with water (250 ml.), add 5 N aqueous HCl (2 ml.), cool with an ice-bath and add 37% aqueous formaldehyde solution (17 ml.). With stirring and cooling drip in a solution of potassium cyanide (10.9 g.) in water (60 ml.). Remove the cooling bath, stir at room temperature for 1 hour, add diethyl ether and stir a further 2 hours. Extract with diethyl ether, then wash, dry and evaporate the extract in vacuo to obtain the intermediate dl-[(1-[hydroxymethyl]-2-phenylethyl)amino] acetonitrile. Without further purification dissolve the product in ethyl alcohol (30 ml.), add water (150 ml.) followed by 5 N aqueous HCl (134 ml.) and stir until clear. Cool (ice-salt bath) and stir, then drip in a solution of sodium nitrite (23.05 g.) in water (120 ml.). Continue stirring for 4 hours while allowing the reaction to warm up to room temperature. Add diethyl ether and stir 1 hour more. Extract with diethyl ether, then wash, dry and evaporate the extract in vacuo. Dissolve the resulting oil in methylene chloride-diethyl ether, treat with decolorizing carbon, filter and evaporate in vacuo to obtain the intermediate dl-N-nitroso-N-[1-(hydroxymethyl)-2-phenylethyl]amino acetonitrile as an oil. Dissolve the oil in ethylacetate, add 5 N isopropanolic —HCl (35 ml.) and let stand to crystallize. Filter to obtain 21.4 g. of the title product, m.p. 158°–160° C. (dec.). Further purify a sample (4.00 g.) by dissolving in methylene chloride containing a little methanol, treating with decolorizing carbon, filtering and replacing the solvent with acetone by boiling on the steam-bath. Cool, then filter the pure title product, 3.49 g.; m.p. 158°–160° C. (dec.).

Analysis for: $C_{11}H_{14}ClN_3O_2$: Calculated: C, 51.67; H, 5.52; N, 16.43; Cl, 13.87%, Found: C, 52.01; H, 5.89; N, 16.50; Cl, 14.13%

EXAMPLE 2 dl-3-[1-(Hydroxymethyl)-2-phenylethyl]-N-[(phenylamino)carbonyl]syndone imine Stir dl-5-amino-3-[1-(hydroxymethyl)-2-phenylethyl]-1, 2,3-oxadiazolium chloride (5.114 g.) with isopropanol (30 ml.), cool with an ice-bath, then add anhydrous sodium acetate powder (1.64 g.). Stir for 15 minutes, then drip in phenylisocyanate (2.38 g. = 2.17 ml.). Stir for 15 minutes, then remove the ice-bath and continue stirring for 5 hours at room temperature. Filter to obtain 4.7 g. of the crude title product. Dissolve the solid in methylene chloride containing a little methanol, treat with decolorizing carbon, filter then replace the solvents with isopropanol by boiling on the steam-bath. Cool and let crystallize, then filter to obtain 2.055 g., m.p. 137°–141° C. Redissolve the solid in methylene chloride, treat with decolorizing carbon, filter and evaporate the solvent in vacuo. Cover the resulting oil with diethyl ether, then add a little isopropanol to redissolve. Let stand, then filter to obtain 1.888 g. of the pure title product, m.p. 137°–141° C. (dec.).

Analysis for: $C_{18}H_{18}N_4O_3$: Calculated: C, 63.89; H, 5.36; N, 16.56%; Found: C, 63.75; H, 5.17; N, 16.62%

Activity Counts: 788 at 10 mg/kg.; 333 at 1 mg/kg.

EXAMPLE 3 dl-N-[(4-Chlorophenylamino)carbonyl]-3-[1-(hydroxymethyl-2-phenylethyl]sydnone imine Stir dl-5-amino-3-[1-(hydroxymethyl)-2-phenylethyl]-1, 2,3-oxadiazolium chloride (5.114 g.) with isopropanol (50 ml.), cool with an ice-bath, then add anhydrous sodium acetate powder (1.61 g.) followed by 4-chlorophenylisocyanate (2.28 g.) and stir at room temperature for 6.5 hours. Filter, then stir the solid with a mixture of chloroform (100 ml.) and acetone (25 ml.). Filter, evaporate the filtrate in vacuo, then dissolve the resulting residue in hot isopropanol (50 ml.), add cyclohexane and boil to reduce volume. Dilute again with cyclohexane and let cool to crystallize. Filter to obtain 2.258 g. of pure title product, m.p. 154°–156° C.

Analysis for: $C_{18}H_{17}ClN_4O_3$: Calculated: C, 57.99; H, 4.60; N, 15.03%; Found: C, 57.72; H, 4.71; N, 14.97%

Activity Counts: 588 at 10 mg/kg.

EXAMPLE 4

1-N-Nitroso-N-[1-(hydroxymethyl)-2-phenylethyl]aminoacetonitrile

Cover L-2-amino-3-phenyl-1-propanol (20.00 g.) with water (150 ml.), cool with an ice-bath and add 5 N aqueous HCl (26.5 ml.) then stir until clear. Add 37% aqueous formaldehyde solution (12 ml.), then with cooling and stirring drip in a solution of potassium cyanide (8.59 g.) in water (30 ml.). Continue stirring for 3 hours, allowing the reaction to warm up to room temperature, then add ethylacetate and stir. Filter, then reextract the filtrate with ethylacetate. Wash, dry and evaporate the combined extracts in vacuo to obtain the crude intermediate, 1-[(1-hydroxymethyl]-2-phenylethyl)amino]acetonitrile. Cover this with water (150 ml.), ethanol (50 ml.) and 5 N aqueous HCl (106 ml.) and stir until clear. Cool (ice-salt bath) and stir while dripping in a solution of sodium nitrite (18.2 g.) in water (80 ml.). Stir the reaction for 5 hours, allowing to warm to room temperature. Filter and dry to obtain 21.0 g. of crude title product, m.p 93°–96° C.

Dissolve 1.00 g. of the above solid in methylene chloride, treat with decolorizing carbon, filter, then boil to low volume on the steam-bath and replace with diethyl ether by boiling. Let stand, then filter to obtain 0.567 g. of pure title product, m.p. 105°–107° C. $[\alpha]_D^{24.5°}$ C. = −118.59° (1.015% in methanol).

Analysis for: $C_{11}H_{13}N_3O_2$: Calculated: C, 60.26; H, 5.98; N, 19.17%; Found: C, 60.16; H, 6.01; N, 19.00%

EXAMPLE 5

1-5-Amino-3-[1-(hydroxymethyl)-2-phenylethyl]-1,2,3-oxadiazolium chloride

Dissolve 1-N-nitroso-N-[1-(hydroxymethyl)-2-phenylethyl]-aminoacetonitrile (16.20 g.) in ethylacetate, treat with 5 N isopropanolic-HCl (15 ml.) and let stand to crystallize. Filter to obtain 17.85 g. of the crude title product, m.p. 162°–166°; $[\alpha]_D^{24}$ = −144.3° (1.265% in methanol). Dissolve 2.70 g. of the crude product in methylene chloride, adding enough methanol to solubilize. Treat the solution with decolorizing carbon, filter, then boil the filtrate on the steam-bath and replace the solvents with isopropanol by boiling. Let cool and stand, then filter to obtain 1.598 g. of pure title product, m.p. 172.0°–173.5° C. (dec.); $[\alpha]_D^{26}$ = −164.87° (0.94% in methanol).

Analysis for: $C_{11}H_{14}ClN_3O_2$: Calculated: C, 51.67; H, 5.52; N, 16.43; Cl, 13.87%; Found: C, 51.36; H, 5.51; N, 16.74; Cl, 13.95%

EXAMPLE 6

1-3-[1-(hydroxymethyl)-2-phenylethyl]-N-[(phenylamino)carbonyl]-sydnone imine Stir 1-5-amino-3-[1-(hydroxymethyl)-2-phenylethyl]-1,2,3-oxadiazolium chloride (5.114 g.) with isopropanol (30 ml.), then cool with an ice-bath and add anhydrous sodium acetate powder (1.64 g.) followed by phenylisocyanate (2.40 g. = 2.20 ml.). Continue stirring, cold, for 1 hour, then remove the ice-bath and stir at room temperature for 2 hours. Let stand overnight, then filter to obtain 5.8 g. of crude title product. Dissolve the solid in methylene chloride containing a little methanol, treat with decolorizing carbon, filter, then evaporate in vacuo. Boil the resulting oil with diethyl ether containing a little isopropanol until crystallization begins, then let stand to cool. Filter to obtain 4.303 g. of the title product, m.p. 149°–155°; $[\alpha]_D^{26} = -252°$ (1.23% in methanol). Dissolve the solid in methylene chloride containing a little methanol, treat with decolorizing carbon, filter, then replace the solvents with isopropanol by boiling on the steam bath. Let cool, then filter to obtain 3.086 g. of the pure title product, m.p. 157°–160° C. $[\alpha]_D^{26} = -265.3°$ (0.995% in methanol).

Analysis for: $C_{18}H_{18}N_4O_3$: Calculated: C, 63.89; H, 5.36; N, 16.56; Found: C, 63.62; H, 5.46; N, 16.73

Activity Counts: 913 at 10 mg/kg.

EXAMPLE 7

1-N-[(4-Chlorophenylamino)carbonyl]-3-[1-(hydroxymethyl)-2-phenylethyl] sydnone imine Following the procedure of Example 3 with the exception that 1-5-amino-3-[1-(hydroxymethyl)-2-phenylethyl]-1,2,3-oxadiazolium chloride is employed in lieu of the racemic mixture as the initial reactant affords the title compound, m.p. 164°–166° C.

Analysis for: $C_{18}H_{17}ClN_4O_3$: Calculated: C, 57.99; H, 4.60; N, 15.03; Found: C, 58.01; H, 4.77; N, 15.19

Activity Counts: 1272 at 10 mg/kg; 893 at 1 mg/kg.

What is claimed is:

1. A compound of the formula:

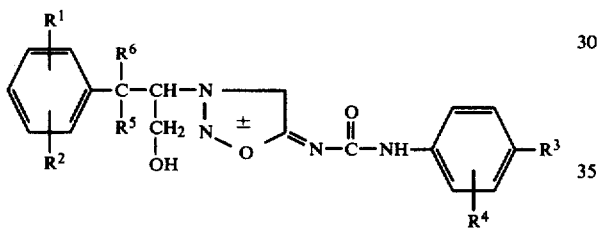

in which
R¹ and R² are, independently, hydrogen, alkyl of 1 to 6 carbon atoms, alkoxy of 1 to 6 carbon atoms, halo, perfluoroalkyl of 1 to 3 carbon atoms, nitro, alkanoyl of 2 to 4 carton atoms or alkoxycarbonyl of 2 to 4 carbon atoms;
R³ is hydrogen, halo, nitro or alkanoyl of 2 to 4 carbon atoms;
R⁴ is hydrogen, halo, nitro or perfluoroalkyl of 1 to 3 carbon atoms;
R⁵ and R⁶ are, independently, hydrogen, methyl or ethyl;
or a non-toxic acid addition salt thereof.

2. A compound of claim 1 of the formula:

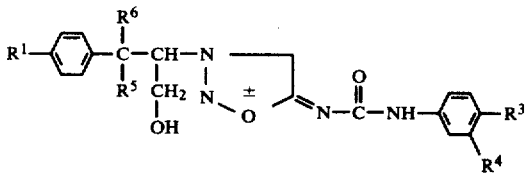

in which
R¹ is hydrogen, alkyl of 1 to 6 carbon atoms, alkoxy of 1 to 6 carbon atoms, halo, perfluoroalkyl of 1 to 3 carbon atoms, nitro, alkanoyl of 2 to 4 carbon atoms or alkoxycarbonyl of 2 to 4 carbon atoms;
R³ is hydrogen, halo, nitro or alkanoyl of 2 to 4 carbon atoms;
R⁴ is hydrogen or halo;
R⁵ and R⁶ are, independently, hydrogen, methyl or ethyl;
or a non-toxic acid addition salt thereof.

3. An 1-enantiomorph of claim 1 of the formula:

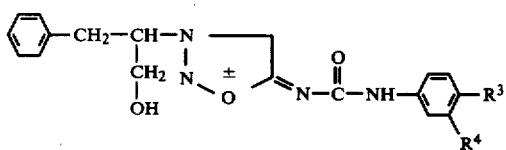

in which
R³ is hydrogen, halo, nitro or alkanoyl of 2 to 4 carbon atoms;
and
R⁴ is hydrogen or halo;
or a non-toxic acid addition salt thereof;

4. A compound of claim 1 which is 3-[1-(hydroxymethyl)-2-phenylethyl]-N-[(phenylamino)carbonyl]sydnone imine.

5. A compound of claim 4 which is 1-3-[1-hydroxymethyl)-2-phenylethyl]-N-[(phenylamino)carbonyl]-sydnone imine.

6. A compound of claim 1 which is N-[(4-chlorophenylamino)carbonyl]-3-[1-(hydroxymethyl)-2-phenylethyl]sydnone imine.

7. The compound of claim 6 which is 1-N-[(4-chlorophenylamino)carbonyl]-3-[1-(hydroxymethyl)-2-phenylethyl]sydnone imine.

* * * * *